United States Patent [19]

Archibald

[11] 4,030,501

[45] June 21, 1977

[54] HIGH FREQUENCY-HIGH VOLTAGE LEVEL ELECTROSURGICAL UNIT

[75] Inventor: G. Kent Archibald, White Bear Lake, Minn.

[73] Assignee: Minnesota Mining and Manufacturing Company, St. Paul, Minn.

[22] Filed: Jan. 26, 1976

[21] Appl. No.: 652,144

[52] U.S. Cl. .................. 128/303.14; 128/303.17
[51] Int. Cl.² ................ A61B 17/36; A61N 3/02
[58] Field of Search ............... 128/303.14, 303.17, 128/303.13, 303.18, 421–423

[56] References Cited

UNITED STATES PATENTS

| | | | |
|---|---|---|---|
| 3,478,744 | 11/1969 | Leiter | 128/303.14 |
| 3,675,655 | 7/1972 | Sittner | 128/303.14 |
| 3,699,967 | 10/1972 | Anderson | 128/303.14 |
| 3,885,569 | 5/1975 | Judson | 128/303.14 |
| 3,952,748 | 4/1976 | Kaliher | 128/303.14 |

Primary Examiner—Robert W. Michell
Assistant Examiner—Lee S. Cohen
Attorney, Agent, or Firm—Cruzan Alexander; Donald M. Sell; G. Brian Pingel

[57] ABSTRACT

A transistorized electrosurgical unit for selectively providing high fequency, high voltage level, cutting or coagulation currents to electrosurgical patient electrodes and including a plurality of parallel connected power stages actuatable by a control signal to supply power to an output transformer connected to the electrodes, which power stages each include a power transistor biased in a nonsaturated condition and connected in series with a constant current transistor, and a signal source transistor connected to such power transistor to supply a switching signal thereto and to serve as a current flow path whenever current flow through the power transistor is interrupted.

6 Claims, 2 Drawing Figures

4,030,501

HIGH FREQUENCY-HIGH VOLTAGE LEVEL ELECTROSURGICAL UNIT

BACKGROUND OF THE INVENTION

1. Field of the Invention

The present invention relates in general to transistorized electrosurgical units and more specifically to such units that selectively provide high frequency, high voltage level, cutting or coagulation currents.

2. Description of the Prior Art

A wide variety of electrosurgical units for generating cutting and coagulation currents are known in the art. The earliest of these units include spark gaps and/or electronic circuits with vacuum tubes and they have provided reasonably good high frequency surgical currents at high power levels. However, a major drawback with spark gap and the tube units is that they are inherently unreliable and bulky. Recently, various electrosurgical unit manufacturers have attempted to provide transistorized units.

Various types of transistorized units are shown in U.S. Pat. Nos. 3,885,569, 3,699,967 and 3,675,655. The primary advantage that transistorized units have provided over tube or spark gap type units in that they are significantly smaller in size and lighter in weight than spark gap or tube units and they are more reliable. However, a problem with heretofore known transistorized units is that none are able to provide both high voltage level operation as well as high frequency currents. This is because power transistors with unusally high voltage ratings must be employed to provide the most desirable voltage levels for for optimum operation. Accordingly, in prior art circuits, rapid switching of such high voltage power transistors has not been achieved. While lower power transistors can be and are employed in units presently on the market in order that high frequency currents can be achieved, such units suffer from a lack of sufficient voltage for most effective operating conditions.

The present invention provides a transistorized electrosurgical unit that not only generates high frequency cutting and coagulation currents but also provides high voltage level outputs.

SUMMARY OF THE INVENTION

The present invention provides an electrosurgical unit for selectively supplying high frequency, high voltage level alterating cutting or coagulation currents, which unit is driven by a plurality of power stages that each include a power transistor connected in series with a constant current means, a bias voltage source that prevents the power transistor from operating in a saturated condition, and a signal source connected with such power transistor to control the operation thereof and to also serve as a current flow path whenever current flow through the power transformer is interrupted Each signal source is formed of a transistor, the operation of which is controlled by a control signal fed to the base thereof. The power transistors of the power stages are all biased in such fashion that the signal sources provide an emitter drive to the power transistors. In this way, the signal sources switch the power transistors rapidly on and off in order that high frequency surgical currents will be supplied by the unit. Accordingly, at such time that the signal source transistors are in an off condition, current is supplied through the power transformer and the power transistors to the constant current means, and at such times that the power transistors are in an off condition the signal source transistors supply current to the constant current means.

The power transistors are biased so that the voltage potential of their bases is always less than the voltage potentials existing at their collectors in order that the power transistors are never operated in a saturated condition. In this way, a constant current is provided through the power transformer; this prevents extraneous ripple voltages from being applied across the primary winding thereof precluding the generation of undesirable low frequency currents from being applied to the patient.

DESCRIPTION OF THE PREFERRED EMBODIMENT

Figure 1:
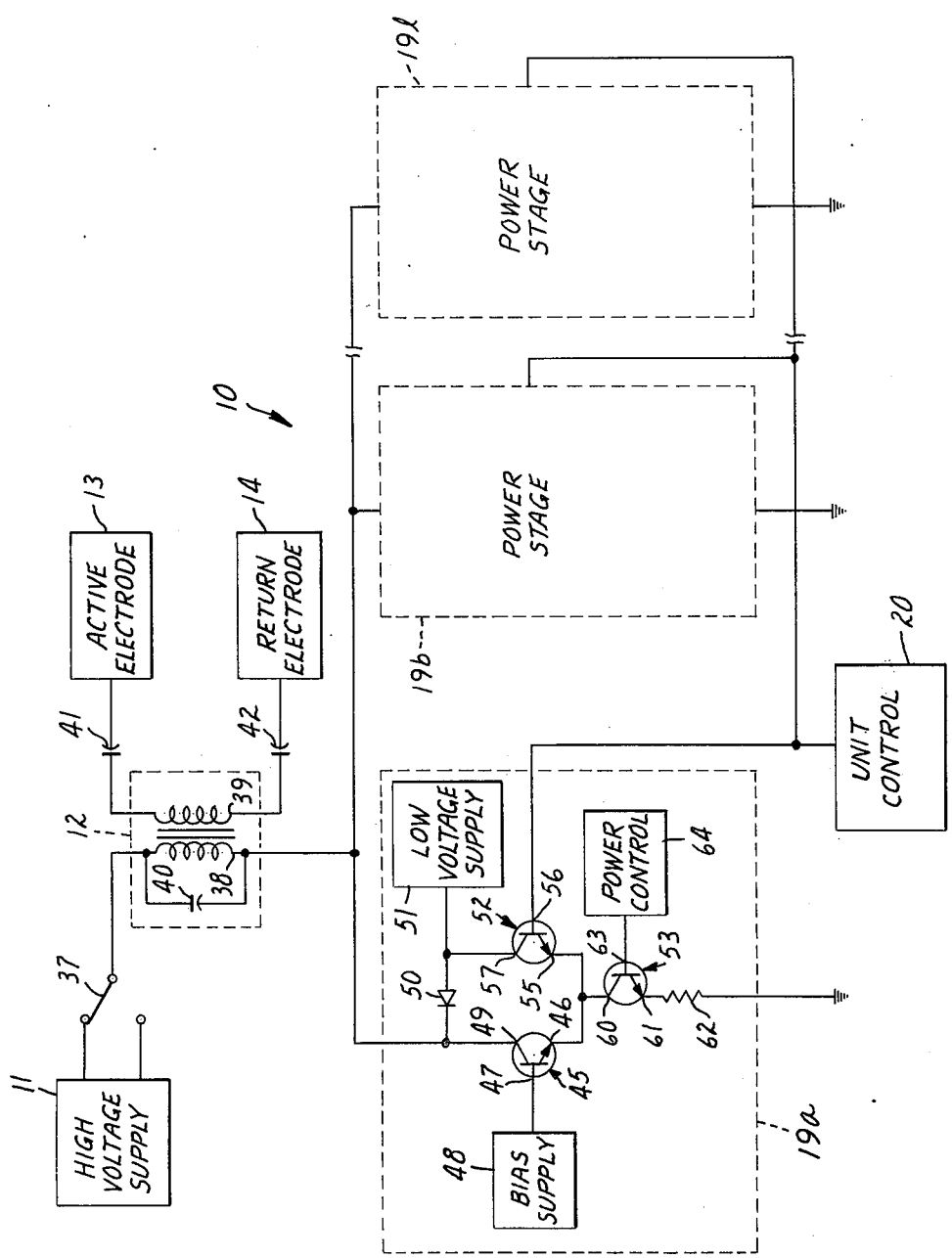
FIG. 1 is a schematic and block diagram of electronic circuitry forming a preferred embodiment of the electrosurgical unit of the present invention.

A preferred embodiment of an electrosurgical unit 10 of the present invention is shown in FIG. 1. The unit 10 is adapted to selectively provide high frequency alternating cutting currents or high voltage level, high frequency alternating coagulation currents that are substantially free of low frequency variations due to line voltage fluctuations in order that surgical operations may be effectively performed on patients.

The main components of the unit 10 are a high voltage supply 11, a power transformer 12, an active electrode 13, a return electrode 14, 12 power stages 19a–l and a control unit 20 with a mode selector switch and drive circuitry that includes a square wave generator. The unit 10 is designed to provide approximately a maximum output electrode voltage of 6000 volts peak-to-peak open circuit in a coagulation mode and approximately 1400 volts peak-to-peak open circuit in a cutting mode. The unit 10, as shown and described, includes 12 power stages, but it should be understood that this number of power stages is merely preferable and is not essential to the present invention. The use of 12 power stages insures that the unit 10 will be able to supply adequate power for its intended use and will not burn out even if the active and return electrodes are shorted together for a short interval.

Figure 2:
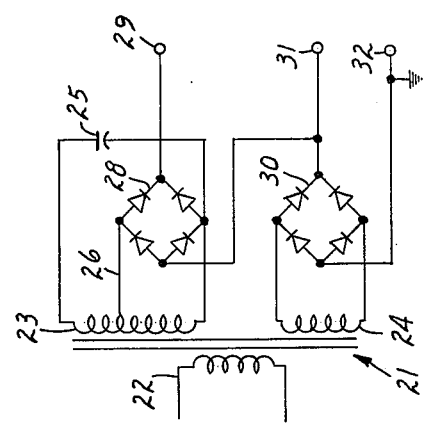
FIG. 2 is a schematic diagram of the high voltage supply shown in FIG. 1.

As shown in FIG. 2, the high voltage supply 11 is preferably formed of a ferroresonance transformer 21 having a first primary winding 22 for connecting to standard a.c. power lines and two secondary windings 23 and 24. A capacitor 25 is connected across the output terminals of the winding 23 and such winding also has a tap 26. A full wave rectifier bridge 28 is connected to one of the output terminals and the tap 26 of the winding 23 to provide a d.c. voltage of approximately 375 volts at an output terminal 29. Another full wave rectifier bridge 30 is connected across the winding 24 to furnish approximately 130 volts at an output terminal 31. Terminal 32 of the bridge 30 is grounded.

The advantage of using the ferroresonance transformer 21 instead of a standard transformer is that the capacitor 25 serves to maintain voltages across the secondary windings 23 and 24 uniform in spite of fluctuations in the line voltage supplied to the primary winding 22. In this way wide variations in supply voltage do not cause increased power dissipation across the power stages 19a–l, or reduce the output impedance range to which the unit will supply power.

Referring again to FIG. 1, a single pole mode select relay 37 that is actuated by the control unit 20 is employed for selecting the desired output voltage of the supply 11 for the particular surgical operation to be performed. The relay 37 is connected in series with a primary winding 38 of the power transformer 12. Preferably, a capacitor 40 is bridged across the primary winding 38 to provide a circuit tuned to the frequency desired for optimum surgical operation.

The transformer 12 also includes a secondary winding 39 connected in typical series fashion to the active electrode 13 and the return electrode 14. Blocking capacitors 41 and 42 are connected in series with the active and return electrodes respectively to prevent spurious low frequency currents from circulating in the patient circuit. The amount of power provided to the secondary winding 39 of the transformer 12 is directly dependent upon the operation of the power stages 19a–l. Each of the power stages 19a–l is connected in parallel with one another and in series with the transformer primary winding 38.

For purposes of simplicity and clarity, only the power stage 19a is shown in FIG. 1 in schematic form because the remaining power stages are identical to stage 19a. As shown, the power stage 19a includes a power switching transistor 45 having a current output emitter terminal 46, a control base terminal 47 that is connected preferably to a 15 volt bias supply 48, and an input current collector terminal 49 that is connected to the transformer primary winding 38. The collector 49 is also connected via a clamping diode 50 to preferably 22 volt low voltage supply 51 for a purpose to be described below. The emitter 46 of the transistor 45 is connected to both a switching transistor 52 that serves as a drive signal source for the transistor 45 and to a transistor 53 serving as a constant current means that draws current from either the transistor 45 or the transistor 52. The transistor 52 includes an emitter terminal 55 connected to the emitter 46 of the transistor 45, a base terminal 56 connected to the drive circuitry of the control unit 20, and a collector terminal 57 connected to the low voltage supply 51.

The transistor 53 includes a collector terminal 60 connected to the emitters 46 and 55 of the transistors 45 and 52 respectively, an emitter terminal 61 connected through resistor 62 to ground, and a base terminal 63 connected to a variable power voltage supply 64 that furnishes a bias voltage to the base of the transistor 53 to permit only a desired amount of current flow therethrough as well as through the power transformer 12. Such current regulation of the transistor 53 is achieved because the amount of current that flows through the transistor 53 is directly proportional to the voltage applied to the base of the transistor 53. Accordingly the power control 64 may be adjusted to provide various voltages to the base 63 of the transistor 53 in order to increase or decrease its current conduction. Although the use of the control 64 is preferable, current control of the transistor 53 may also be gained by the use of a variable resistor 62.

The unit 10 is activated by keying the mode selector switch of the unit control 20 to the desired surgical mode of operation. According to the mode selected, the mode selector circuitry of the unit control 20 actuates the mode select relay 37 to provide the appropriate voltage from the high voltage supply 11 to the power transformer 12. Concurrently, the drive control circuitry of the unit control 20 applies a control voltage signal to the base of the transistor 52, which signal is a square wave that alternates between a maximum of 22 volts and a minimum of 9 volts.

When a 9 volts pulse of the drive signal from the unit control 20 is supplied to the base 56, the transistor 52 is essentially back biased to an off condition and the transistor 45 begins conducting. When a 22 volt pulse from the control unit 20 is supplied to the base 56 of the transistor 52, such transistor begins conducting and thereby increases the voltage at the emitter 46 of the transistor 45. This voltage increase causes the transistor 45 to turn off. Accordingly, the transistor 52 acts as a signal source to rapidly switch the transistor 45 on and off by means of the application of a drive signal to the emitter of the transistor 45 and thereby provides the high frequency alternating surgical current of the unit 10 of approximately 500 kilohertz. Moreover, the transistor 52 serves as a current source to the transistor 53 at such times when the transistor 45 is not conducting.

The clamping diode 50 together with the low voltage supply 51 enhances rapid switching of the transistor 45 by clamping the collector 49 at a greater positive potential than that at the base 47 in order that the transistor 45 never reaches a saturated condition. By preventing saturation of the transistor 45, excess charges are prevented from building up in its base 47. As is well known in the art, excess charge accumulation in the base of a transistor inhibits rapid switching because a transistor will not turn off until such excess charges are reduced.

A second advantage of preventing the transistor 45 from saturating is that when the transistor 45 operates in a nonsaturated condition, it will also operate in a constant current mode in order that constant current will flow through the entire power stage 19a. Because the current through the power stage 19a and the remaining power stages 19b–l as well is held substantially stable, this means that a constant current will also flow through the power transformer as well, therefore precluding the generation of unwanted low frequency currents that are harmful to the patient. Thus, nonsaturation operating of the transistor 45 is critical to proper operation of the unit 10.

The control voltage signal provided by the unit control 20 is a continuous square wave in order that a continuous a.c. signal is provided for the cutting mode of the unit 10. However, for use of the unit 10 is a coagulation mode, a continuous signal is undesirable and instead spaced apart cycles of pulses are provided by the unit control 20 to the transistor 52. As a consequence, the current provided to the active electrode 13 is in the form of spaced apart bursts of energy.

For providing narrow area coagulation, these burst of energy should be spaced apart at various length time spans but it is preferable that the time between energy bursts be approximately 60 microseconds. For providing wide area coagulation, I have found that in addition to reducing the time spans between the bursts of energy to 30 microseconds, relatively wide time gaps must be introduced between groups of energy bursts. Such gaps should fall in the range of approximately 1,000 microseconds and preferably should be 6,000 microseconds. Thus, an optimum wide area coagulation current will consist of groups of energy bursts spaced apart from one another by 6,000 microseconds with each such group including at least several energy bursts spaced apart from one another by 30 microseconds.

In an exemplary embodiment of the electrosurgical unit of the present invention, components identified as follows were used.

| | |
|---|---|
| Diode 50 | 1200 PVI, 1 Amp |
| Transistor 45 | MJ 3480 |
| Transistor 52 | D 44H5 |
| Transistor 53 | TIP 3055 |
| Resistor 62 | 2 Ohm, 10 Watt |

What we claim is:

1. In an electrosurgical unit for selectively providing high frequency, cutting currents or high voltage level coagulation currents to the body of a patient by means of electrosurgical patient electrodes which are driven by power stages actuatable by a control signal, which unit includes at least a pair of patient electrodes, a unit control means for supplying said control signal, a source of high voltage, a power transformer having a primary winding connected in series with said high voltage source and a secondary winding connected in series with said electrodes, and a plurality of power stages that are connected in parallel with one another and in series with said transformer primary winding, said power stages each including:

a power switching element having an input terminal connected to one side of the power transformer primary winding, an output terminal and a control terminal;

a constant current means connected in series with the output terminal of said switching element;

a power control means for variably adjusting the amount of current flowing through said current means;

a bias supply means connected to the control terminal of said switching element for supplying a bias voltage thereto;

a voltage source clamping means connected to the input terminal of said switching element to supply a sufficient level of voltages to said input terminal that said switching element is prevented from operating in a saturated state in order that each of the entire power stages has a constant current flowing therethrough; and a signal source means that is driven by said control signal and is connected to the output terminal of said switching element to control the actuation thereof and supply current to said current means whenever current flow through said switching element is interrupted.

2. In an electrosurgical unit as recited in claim 1 wherein said source of high voltage for said unit is formed of a ferroresonance transformer.

3. In an electrosurgical unit as recited in claim 1 wherein a resistor is connected to ground and said constant current means is a transistor having a collector terminal connected to the output terminal of said switching element, an emitter terminal connected by said resistor to ground, and a base terminal that is connected to the power control means whereby the current flow through said transistor may be adjusted by varying said power control means.

4. In an electrosurgical unit as recited in claim 1 wherein said clamping means supplies a voltage to the input terminal of said switching element that is maintained at a higher level than the voltage supplied to the control terminal of said switching element by said bias supply means.

5. In an electrosurgical unit for selectively providing high frequency, cutting currents or high voltage level coagulation currents to the body of a patient by means of electrosurgical patient electrodes, which unit includes at least a pair of patient electrodes a source of high voltage, and a power transformer having a primary winding connected in series with said high voltage source and a secondary winding connected in series with said electrodes, said unit further including:

a plurality of power stages connected in parallel with one another and in series with said transformer primary winding; and a control signal source means for actuating each of said power stages for predetermined periods of time so that spaced apart groups of spaced apart bursts of energy are generated, which groups of bursts of energy are spaced from one another by at least 1,000–10,000 microseconds in order to achieve wide area coagulation.

6. In an electrosurgical unit as recited in claim 5 wherein said groups of bursts of energy are generated at no less than approximately 6,000 microseconds apart.

* * * * *

UNITED STATES PATENT AND TRADEMARK OFFICE
CERTIFICATE OF CORRECTION

PATENT NO. : 4,030,501
DATED : JUNE 21, 1977
INVENTOR(S) : G. KENT ARCHIBALD

It is certified that error appears in the above-identified patent and that said Letters Patent are hereby corrected as shown below:

Column 1, line 18, omit "the";

Column 1, line 31, change "unusally" to -- unusually --;

Column 1, line 49, change "alterating" to -- alternating --;

Column 4, line 58, change "burst" to -- bursts --;

Column 4, line 67, after "seconds" insert -- to 10,000 microseconds --;

Column 5, line 48, change "voltages" to -- voltage --;

Column 6, line 18, change "neced" to -- nected --.

Signed and Sealed this

Eleventh Day of October 1977

[SEAL]

Attest:

RUTH C. MASON
Attesting Officer

LUTRELLE F. PARKER
Acting Commissioner of Patents and Trademarks